United States Patent
Jon

(10) Patent No.: US 8,469,913 B1
(45) Date of Patent: Jun. 25, 2013

(54) INJURED LIMB PROTECTOR

(75) Inventor: Hermanson Jon, Knoxville, TN (US)

(73) Assignee: Albahealth, LLC, Rockwood, TN (US)

( * ) Notice: Subject to any disclaimer, the term of this patent is extended or adjusted under 35 U.S.C. 154(b) by 101 days.

(21) Appl. No.: 12/816,722

(22) Filed: Jun. 16, 2010

(51) Int. Cl.
*A61F 13/06* (2006.01)

(52) U.S. Cl.
USPC ............... 602/61; 602/60; 602/62; 602/63; 2/16; 2/22; 2/24

(58) Field of Classification Search
USPC ............... 602/60–66; 128/99.1, 106.1, 107.1, 128/111.1, 117.1, 894; 5/636, 646; 2/16–17, 2/201, 22, 24, 267
See application file for complete search history.

(56) References Cited

U.S. PATENT DOCUMENTS

| | | | |
|---|---|---|---|
| 3,990,440 A | 11/1976 | Gaylord, Jr. | |
| 4,150,442 A | 4/1979 | Boone | |
| D261,821 S | 11/1981 | Hubbard et al. | |
| RE32,680 E | 5/1988 | Pompa | |
| 4,756,026 A | 7/1988 | Pierce, Jr. | |
| 5,063,919 A | 11/1991 | Silverberg | |
| 5,067,175 A | 11/1991 | Gold | |
| 5,071,698 A | 12/1991 | Scheerder et al. | |
| 5,449,339 A | 9/1995 | Drennan | |
| 5,827,211 A | 10/1998 | Sellinger | |
| 5,882,324 A | 3/1999 | Baranowski | |
| 5,887,277 A | 3/1999 | Lohman | |
| 5,944,683 A | 8/1999 | Baranowski | |
| 5,946,737 A | 9/1999 | Fleege | |
| 5,951,366 A | 9/1999 | Stevens | |
| 5,952,078 A | 9/1999 | Park | |
| 6,005,041 A | 12/1999 | Cook | |
| 6,070,273 A * | 6/2000 | Sgro | 2/455 |
| 6,095,894 A | 8/2000 | Stevens | |
| 6,256,804 B1 | 7/2001 | Stevens | |
| 6,279,160 B1 * | 8/2001 | Chen | 2/24 |
| 6,415,795 B1 * | 7/2002 | Kew | 128/869 |
| 6,625,831 B2 | 9/2003 | Laughlin | |
| 7,299,506 B1 | 11/2007 | Samaroo | |
| 7,608,314 B2 | 10/2009 | Plant | |
| 2005/0273030 A1 * | 12/2005 | Koby et al. | 602/60 |
| 2010/0147722 A1 * | 6/2010 | Datta | 206/440 |

* cited by examiner

*Primary Examiner* — Patricia Bianco
*Assistant Examiner* — Camtu Nguyen
(74) *Attorney, Agent, or Firm* — Baker, Donelson

(57) ABSTRACT

An injured limb protector (10) includes a pad (11), a tubular pad cover (12) surrounding the pad, and a tubular sleeve (13). The pad is a dual density material having an outer layer (16) which is made of a high density material bonded to an inner layer (17) which is made of a low density material. The outer layer is scored or cut to allow manipulation of the pad to conform to an elbow or heel. The pad includes a central portion (19), two oppositely disposed end flaps (22) and two oppositely disposed side flaps (23), which allow it to be formed into a cup-shaped pad. The sleeve is provided with a visible alignment line (26) oriented longitudinally upon the one side (15) of the sleeve to which the pad is mounted.

6 Claims, 3 Drawing Sheets

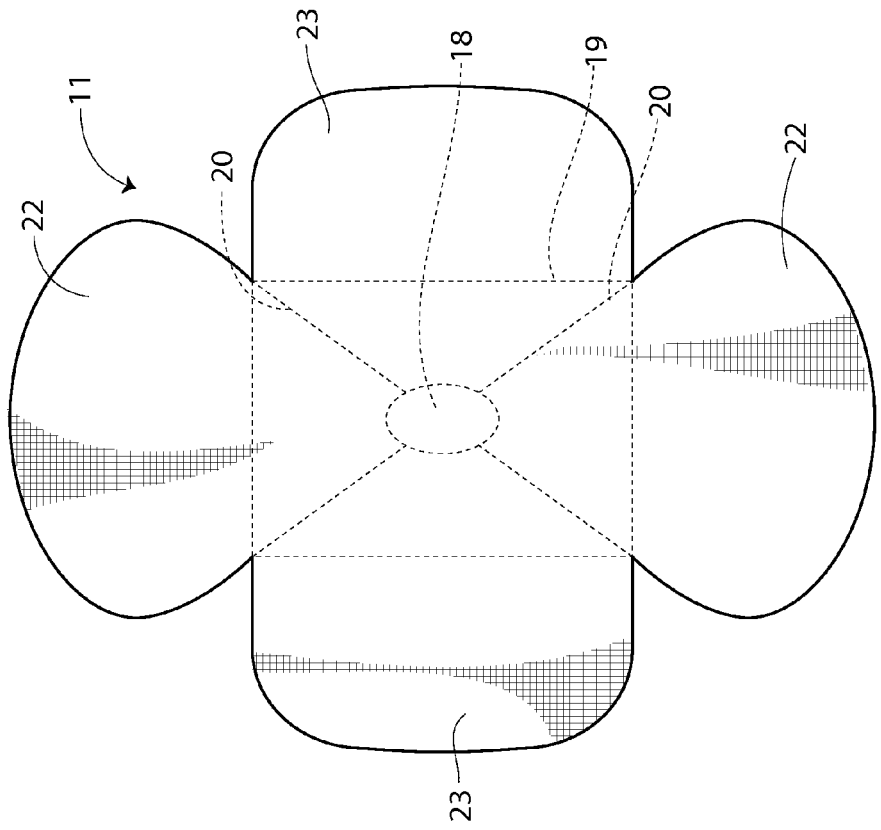
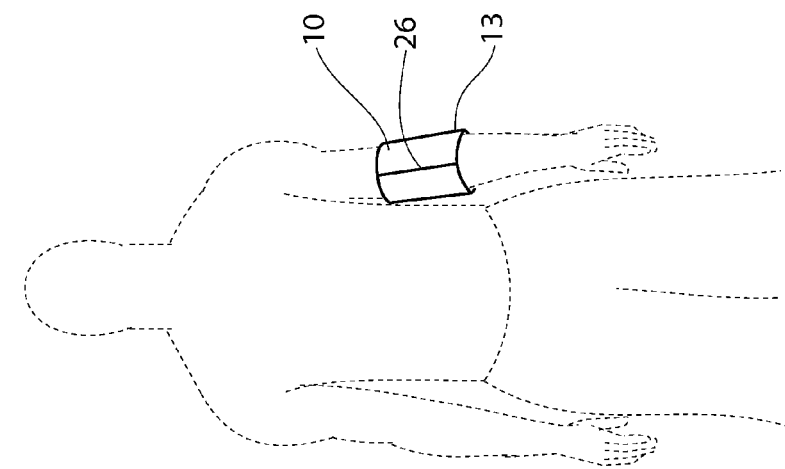

INJURED LIMB PROTECTOR

TECHNICAL FIELD

This invention relates generally to a protector and more specifically to a protector for an injured or compromised limb joint such as the elbow or heel of a person.

BACKGROUND OF THE INVENTION

People often times harm one's elbow or knee resulting in an injury that must be protected from further harm due to subsequent contact. For this reason, the medical field has produced elbow and heel protectors which cushion these joints.

To date, the protectors which have been used in the medical industry have been relatively soft foam pads that are strapped to the injured leg or arm of a person. These pads have not proven to stay in the desired location due to movement of the limb. Also, as the harm to the person may also include an injury to the skin, medical pads must also be able to be worn without aggravating the injury to the wearer's skin.

Accordingly, it is seen that a need remains for an limb protector that remains in place but will not aggravate any injury to the skin. It is to the provision of such therefore that the present invention is primarily directed.

SUMMARY OF THE INVENTION

In a preferred form of the invention an injured limb protector comprises a pad, a pad cover overlaying at least an inward surface of the pad, and an elongated, tubular, stretchable sleeve defining an interior passage. The pad cover is coupled to the sleeve with the pad positioned within the sleeve interior passage, the sleeve having a visible, longitudinally extending aligning line positioned to coincide generally with the longitudinal axis of the pad.

In another preferred form of the invention, an injured limb protector comprises a pad, an elongated tubular pad cover encasing the pad, and an elongated, tubular, stretchable sleeve defining an interior passage. The pad cover is coupled to the sleeve with the pad positioned within the sleeve interior passage.

In yet another preferred form of the invention an injured limb protector comprises a pad having an exterior pad layer having a first density and an interior pad layer bonded to the exterior pad layer, the interior pad layer having a second density less than the exterior pad layer first density. The protector also has a pad cover overlaying at least an inward surface of the pad, and an elongated, tubular, stretchable sleeve defining an interior passage, the pad cover being coupled to the sleeve with the pad positioned within the sleeve interior passage,

BRIEF DESCRIPTION OF THE DRAWING

FIG. 3 is a perspective view of the injured limb protector of FIG. 1, shown donned upon a person's arm.

FIG. 4 is a bottom, plan view of the pad of the injured limb protector of FIG. 1.

DETAILED DESCRIPTION

Figure 1:
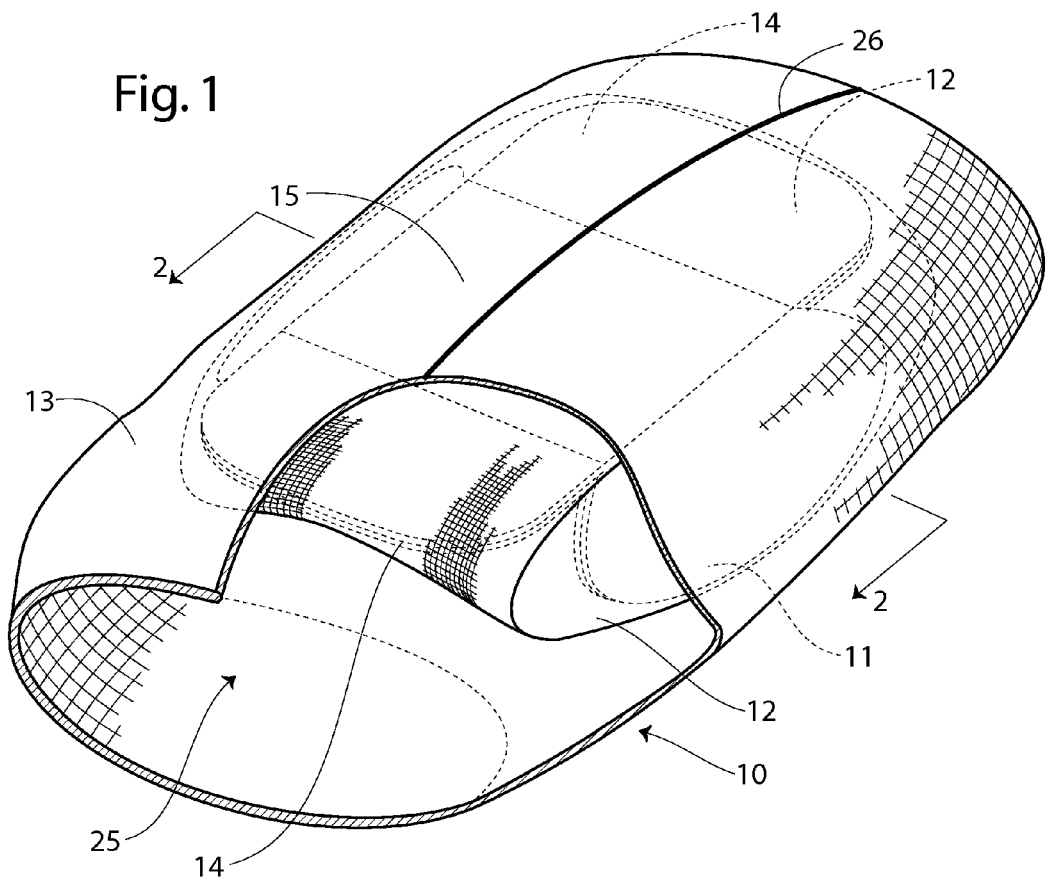
FIG. 1 is a perspective view of a preferred form of the injured limb protector in a preferred form of the invention.
Figure 2:
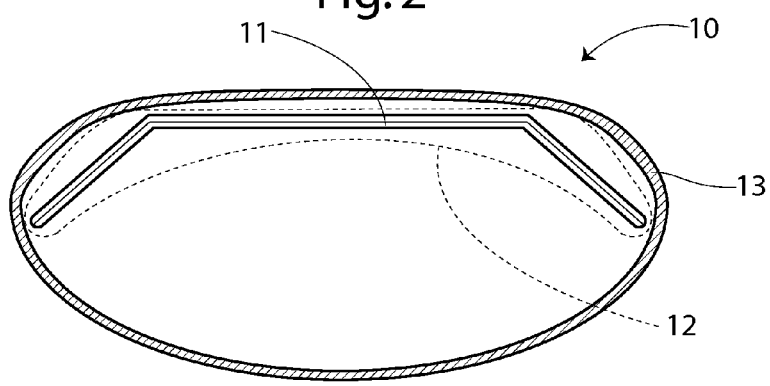
FIG. 2 is a cross-sectional view of the injured limb protector of FIG. 1.

With reference next to the drawings, there is shown an injured limb protector 10 in a preferred form of the invention. The protector 10 includes pad or padding member 11, a tubular pad cover or sheath 12 surrounding the pad 11, and a tubular sleeve 13. The pad cover 12 is mounted at opposite ends 14 to the sleeve 13 so that the pad 11 resides within the interior passage of the tubular sleeve 13 closely adjacent one side 15 of the sleeve.

Figure 5:
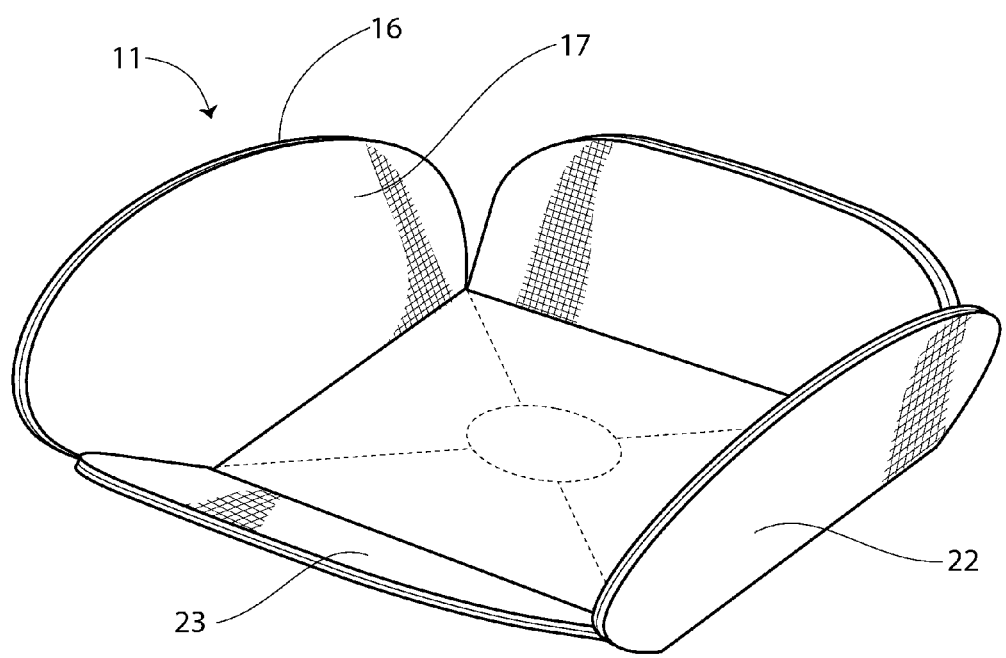
FIG. 5 is a perspective view of the pad of the injured limb protector of FIG. 1.

The pad 11 is a dual density material having an outer, first layer 16 which is made of a high density material, such as polyester foam closed cell material, bonded to an inner, second layer 17 which is made of a low density material, such as a cross linked polyurethane material. The outer layer 16 helps absorb the shock of impact from a direct force, while the inner layer 17 provides a soft conforming profile for the limb positioned against it. The outer layer 16 is scored or cut to allow manipulation of the pad to conform to an elbow or heel. The outer layer scoring includes a centrally located, generally oval 18 surrounded by a rectangle 19 and four diagonal lines 20 extending between the central oval 18 and the outer rectangle 19. About the periphery of the rectangular are two oppositely disposed end flaps 22 and two oppositely disposed side flaps 23. The scoring of the pad allows it to be formed into a bowl-shape or cup-shape, as shown in FIG. 5, so as to protect an elbow or heel residing within the "cup", the term "cup" as used herein is intended to represent an shape having a floor and four sidewalls extending from the floor which may or may not meet at the side edges of the sidewalls. The outer and inner layers 16 and 17 may be bonded together in any conventionally know manner, such as with an adhesive, heat or combination thereof, such as being flame laminated.

The tubular pad cover 12 is made of an antimicrobial or antibacterial treated tubular knit stockinette material of an integrated blend of both spun and filament yarns. Preferably, the material is 100% polyester with 15% of the polyester by weight being an engineered moisture management yarn sold under the brand name Coolwick by Sapona Mills and the remaining 85% by weight of the material being a basic polyester. The material is treated with any type of commonly available antimicrobial materials or may include a small amount, such as 4% by weight, of silver ion treated fibers.

The material properties of the pad cover 12 provide improved moisture management in wicking, absorption, and drying time. For example, as compared to polyester stockinette, this material wicks moisture approximately 28% faster than polyester, absorbs fluids approximately 95% faster than polyester, and dries approximately 9% faster than polyester. Additionally, the antimicrobial property has a kill rate of greater than 98% for a 24 hour wear duration. However, the material still provides a soft fabric face through the use of both spun yarns and high filament count filament synthetic yarns.

The tubular sleeve 13 is made of a knit material having approximately 75% nylon fibers by weight and 25% elastomeric fibers by weight such as Spandex fibers sold under the trade name LYCRA and available from E.I. DuPont de Nemours and Company, Wilmington, Del., USA. The sleeve 13 is stretchable in both the longitudinal and circumferential directions and is adapted to provide a snug fit over the arm or foot of the wearer positioned with the central passage 25 of the tubular sleeve. The sleeve material allows it to be worn for medical applications as a non-adherent retainer. The sleeve is provided with a visible alignment line 26 oriented longitudinally upon the one side 15 of the sleeve 13 to which the pad 11 is mounted. This line may be imprinted upon the sleeve or created through the inclusion of a contrasting colored filament woven into the sleeve.

In use, the limb of a person is passed through the central passage 25 of the tubular sleeve 13 to a position wherein the injured portion resides against the pad 11. If the injured portion is an elbow or heel, the pad may be manipulated to form a cup which surrounds the injured elbow or heel. The soft inner layer 17 provides a soft feel for the person while the outer layer 16 aids in reducing hard from an external impact upon the area.

The antimicrobial properties of the pad cover material aid in odor management and preventing infections, while the material itself again provides for a soft feel for the person.

The sleeve 13 is sized to be snug about the limb of the wearer so that it is maintained in a constant position upon the limb. The central aligning line 26 aids the wearer or a person aiding the wearer to properly aligned the pad upon the wearer's elbow or heel by providing a guideline which is intended to be aligned generally along the centerline of a wearer's elbow or heel, as shown in FIG. 3. As such, the aligning line 26 is positioned to coincide generally with the longitudinal axis of the pad so that is aligned along the centerline of the elbow or heel.

It should be understood that the central alignment line 26 may be color coded or otherwise visually manipulated to provide a visual indication of the protector sizing, i.e., different colors may be used to indicate small, medium or large sized protectors.

It should be understood that as an alternative, the pad cover 12 may be designed to cover only an inwardly facing surface of the pad, i.e., the surface facing the wearer's skin.

It thus is seen that a protector is now provided that allows for greater comfort, alignment, and position retainment. Although the protector has been illustrated and described in its preferred form, it should be understood that many modifications, additions and deletions may be made to that specific form without departure from the spirit and scope of the invention as set forth in the following claims.

The invention claimed is:

1. An injured limb protector comprising:
    a pad having a central longitudinal axis, said pad has an exterior pad layer having a first density and an interior pad layer bonded to said exterior pad layer, said interior pad layer having a second density less than said exterior pad layer first density;
    a fabric pad cover overlaying at least an inward surface of said pad, and
    an elongated, tubular, stretchable sleeve defining an interior passage, said pad cover being coupled to said sleeve with said pad positioned within said sleeve interior passage, said sleeve having an exterior surface having a first color and with a visible, longitudinally extending aligning line of a second color contrasting said first color, said aligning line being positioned to overlay said central longitudinal axis of said pad.

2. The injured limb protector of claim 1 wherein said pad is shaped to form a cup.

3. The injured limb protector of claim 1 wherein said pad cover is tubular, and said tubular pad covering encases said pad.

4. The injured limb protector of claim 3 wherein opposite ends of said tubular pad cover are coupled to said sleeve.

5. An injured limb protector comprising:
    a pad having a central longitudinal axis, said pad includes a central portion, two oppositely disposed end flaps extending from said central portion, and two oppositely disposed side flaps extending from said central portion, wherein said pad is scored at the junction of said central portion with said end flaps and said side flaps;
    a fabric pad cover overlaying at least an inward surface of said pad, and
    an elongated, tubular, stretchable sleeve defining an interior passage, said pad cover being coupled to said sleeve with said pad positioned within said sleeve interior passage, said sleeve having an exterior surface having a first color and with a visible, longitudinally extending aligning line of a second color contrasting said first color, said aligning line being positioned to overlay said central longitudinal axis of said pad.

6. An injured limb protector comprising:
    a pad having a central longitudinal axis;
    a fabric pad cover overlaying at least an inward surface of said pad, and
    an elongated, tubular, stretchable sleeve defining an interior passage, said pad cover being coupled to said sleeve with said pad positioned within said sleeve interior passage, said sleeve having an exterior surface having a first color and with a visible, longitudinally extending aligning line of a second color contrasting said first color, wherein said second color is color coded to indicate the size of the limb protector, said aligning line being positioned to overlay said central longitudinal axis of said pad.

* * * * *